(12) United States Patent
Lange et al.

(10) Patent No.: US 8,617,491 B2
(45) Date of Patent: Dec. 31, 2013

(54) DEVICE FOR RECEIVING A SOLID IN A MEASURING CELL

(75) Inventors: Thomas Lange, Constance (DE); Anette Partheil, Darmstadt (DE)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 363 days.

(21) Appl. No.: 12/993,915

(22) PCT Filed: May 22, 2009

(86) PCT No.: PCT/EP2009/003627
§ 371 (c)(1),
(2), (4) Date: Jan. 19, 2011

(87) PCT Pub. No.: WO2009/141151
PCT Pub. Date: Nov. 26, 2009

(65) Prior Publication Data
US 2011/0113867 A1    May 19, 2011

(30) Foreign Application Priority Data

May 23, 2008   (DE) .......................... 10 2008 024 840

(51) Int. Cl.
*B01L 9/00*   (2006.01)
*B01L 3/00*   (2006.01)

(52) U.S. Cl.
CPC ........................................ *B01L 3/50* (2013.01)
USPC ........................................... 422/561; 422/560

(58) Field of Classification Search
USPC .............. 73/432.1, 865.6, 866; 366/241, 244; 422/224, 560, 561
See application file for complete search history.

(56) References Cited

U.S. PATENT DOCUMENTS 3,620,675 A * 11/1971 Olson ............................... 436/2
3,791,222 A *  2/1974 Goodhart et al. ............... 73/866

(Continued)

FOREIGN PATENT DOCUMENTS

WO    WO 01/38850 A2    5/2001

OTHER PUBLICATIONS

International Search Report of PCT/EP2009/003627 (Nov. 17, 2010).

(Continued)

*Primary Examiner* — David A Rogers

(57) ABSTRACT

A device for the accommodation of a solid in a measuring cell (24), in which the release of the solid can be determined in a solution medium flowing through the measuring cell (24), has an insert (1) which can be introduced into the measuring cell (24) and which has a recess for the accommodation of a pressed disc (31). The recess for the accommodation of the pressed disc (31) is arranged on a side (16) of the insert (1) which faces the inflowing solution medium. A wall surface (32) of the insert (1) which surrounds the recess for the accommodation of the pressed disc (31) is tilted in the flow direction, so that the inflowing solution medium is transported laterally away from the pressed disc (31). The insert (1) has a housing (2) with a hole (3) through it, a sleeve (4) for the accommodation of the pressed disc (31), which can be accommodated in the hole (3), and a closure device (10). The housing (2) and the closure device (10) essentially consist of a plastic material and the sleeve (4) consists of metal. The insert (1) has flow channels (33) through which the solution medium can pass through the insert (1).

9 Claims, 2 Drawing Sheets

(56) References Cited

U.S. PATENT DOCUMENTS

| | | | |
|---|---|---|---|
| 3,801,280 A * | 4/1974 | Shah et al. ................. | 436/2 |
| 3,802,272 A | 4/1974 | Bischoff et al. | |
| 4,305,924 A * | 12/1981 | Piasio et al. ................. | 436/528 |
| 4,335,438 A * | 6/1982 | Smolen ....................... | 702/19 |
| 4,593,563 A * | 6/1986 | Laine et al. ................. | 73/865.8 |
| 4,681,858 A * | 7/1987 | Chaudhari et al. .......... | 436/165 |
| 4,852,400 A * | 8/1989 | Wingrave ................... | 73/152.09 |
| 4,856,909 A | 8/1989 | Mehta et al. | |
| 5,011,662 A * | 4/1991 | Noormohammadi et al. ........................... | 422/68.1 |
| 5,076,107 A * | 12/1991 | Timmermans et al. ........ | 73/866 |
| 5,127,278 A * | 7/1992 | Benz ........................... | 73/866 |
| 5,142,920 A | 9/1992 | Bart et al. | |
| 5,318,183 A * | 6/1994 | Cohen et al. ................. | 206/538 |
| 5,395,323 A * | 3/1995 | Berglund ..................... | 604/84 |
| 5,412,979 A * | 5/1995 | Fassihi ........................ | 73/53.01 |
| 5,476,116 A * | 12/1995 | Price et al. ................... | 137/268 |
| 5,589,649 A * | 12/1996 | Brinker et al. ............... | 73/866 |
| 5,682,001 A * | 10/1997 | Hanson et al. ............... | 73/866 |
| 5,827,984 A * | 10/1998 | Sinnreich et al. ............. | 73/866 |
| 5,958,778 A * | 9/1999 | Kidd ........................... | 436/45 |
| 6,308,584 B1 * | 10/2001 | Benz ........................... | 73/866 |
| 6,336,739 B1 * | 1/2002 | Lee ............................. | 366/143 |
| 6,497,157 B1 | 12/2002 | Viegas et al. | |
| 6,929,782 B1 * | 8/2005 | Ciliberto et al. ............. | 422/561 |
| 7,051,606 B2 * | 5/2006 | Tian et al. .................... | 73/866 |
| 7,237,436 B2 * | 7/2007 | Tian et al. .................... | 73/432.1 |
| 8,281,675 B2 * | 10/2012 | Levin et al. .................. | 73/866 |
| 8,318,506 B2 * | 11/2012 | Burgess et al. ............... | 436/177 |
| 2003/0190350 A1 * | 10/2003 | Franz et al. .................. | 424/465 |
| 2003/0203968 A1 * | 10/2003 | Franz et al. .................. | 514/567 |
| 2004/0228769 A1 * | 11/2004 | Taylor et al. ................. | 422/99 |
| 2007/0036686 A1 * | 2/2007 | Hatamian et al. ............ | 422/102 |
| 2007/0160639 A1 * | 7/2007 | Pantelidis et al. ............ | 424/423 |
| 2008/0138261 A1 * | 6/2008 | Bogner et al. ............... | 422/266 |
| 2008/0165354 A1 * | 7/2008 | Rantanen et al. ............. | 356/301 |
| 2008/0240998 A1 * | 10/2008 | Urbahn et al. ................ | 422/99 |
| 2009/0064768 A1 * | 3/2009 | Alkhawam et al. .......... | 73/64.56 |
| 2009/0165578 A1 * | 7/2009 | Zamloot et al. .............. | 73/864.91 |
| 2009/0185187 A1 * | 7/2009 | Crist et al. ................... | 356/436 |
| 2010/0262381 A1 * | 10/2010 | Zeng ........................... | 702/23 |

OTHER PUBLICATIONS

European Pharmacopoeia 5.4 "Intrinsic Dissolution," pp. 3705-3706.
European Pharmacopoeia 5.6 "Apparent Dissolution," pp. 4438-4439.
V. M. Rao et al., "A Mechanistic Study of Griseofulvin Dissolution into Surfactant Solutions under Laminar Flow Conditions," Journal of Pharmaceutical Sciences, vol. 86, No. 10 (Oct. 1997) pp. 1132-1137.
W. Sun et al., "A Mechanistic Study of Danazol Dissolution in Ionic Surfactant Solutions," Journal of Pharmaceutical Sciences, vol. 92, No. 2 (Feb. 2003) pp. 424-435.
P. J. Missel et al., "Reexamination of Convective Diffusion/Drug Dissolution in a Laminar Flow Channel: Accurate Prediction of Dissolution Rate," Pharmaceutical Research, vol. 21, No. 12 (Dec. 2004) pp. 2300-2306.

* cited by examiner

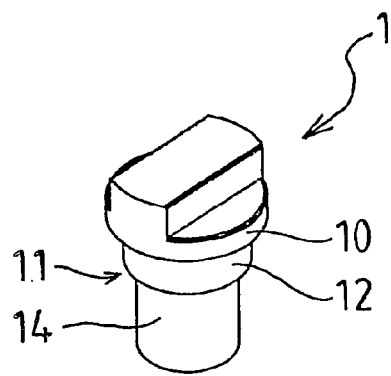
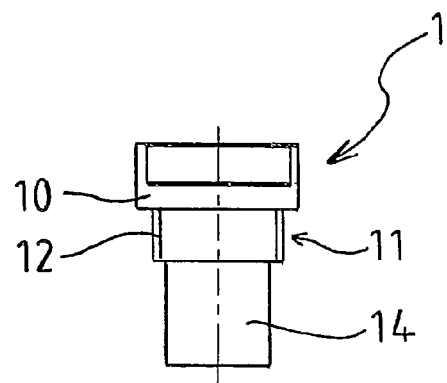
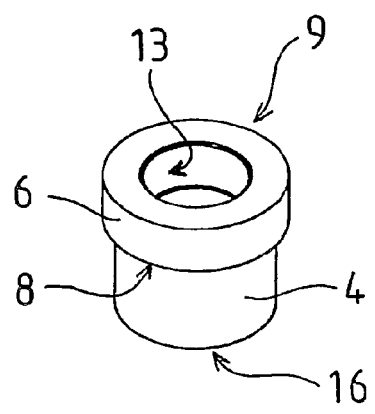
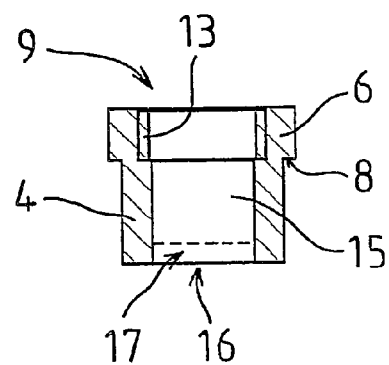
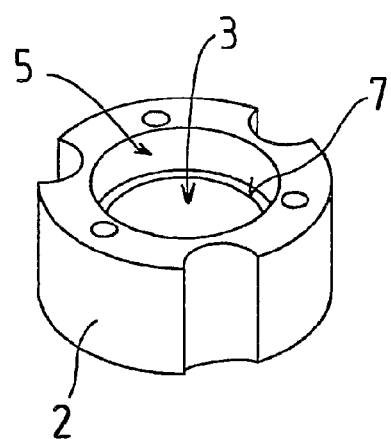
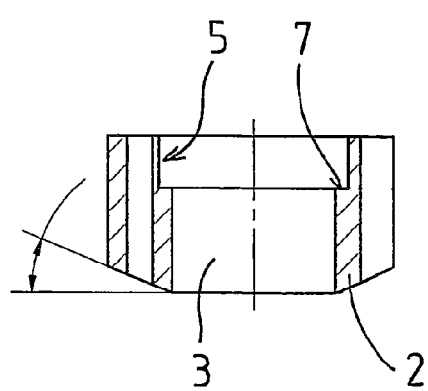
Fig. 1
Fig. 2

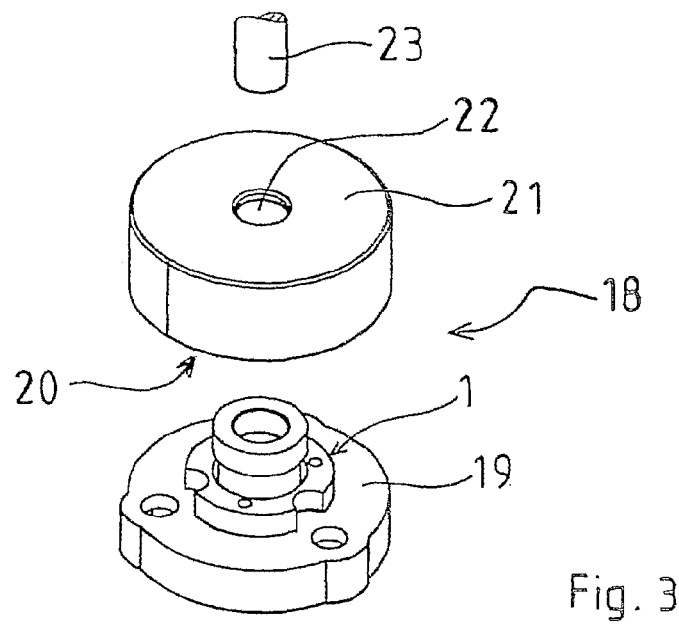
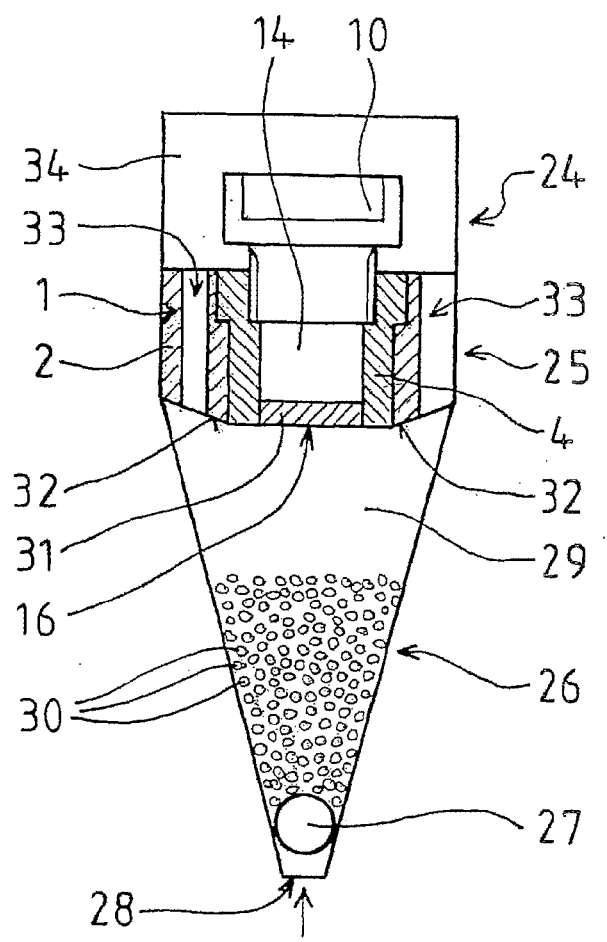

DEVICE FOR RECEIVING A SOLID IN A MEASURING CELL

The invention relates to a device for the accommodation of a solid in a measuring cell, in which the release of the solid can be determined in a solution medium flowing through the measuring cell.

In order to investigate the properties of an active compound and in particular its release rate or dissolution in liquid media, it is known to introduce the active compound in solid form into a suitable measuring cell with a solution medium and to record the amount of active compound released as a function of time. Since the release of an active compound must be taken into account both during the preparation and also during the dosing and administration of pharmaceutical preparations and is often of major importance, various measuring cells and measurement methods have been developed by means of which the measurement results with the greatest possible reproducibility can be determined in order to enable a comparison of measurement results from different experimental series and from different sources. The measuring devices used should advantageously be both simple to operate and at the same time facilitate reliable and precise measurement results.

The release rate of an active compound in the form of a powder, granules or a tablet can be determined using, for example, through-flow measuring cells described in EUROPEAN PHARMACOPOEIA (2.9.3. "dissolution test for solid dosage forms" & 2.9.43. "apparent dissolution"), USP <711> and JP XIV General Tests 15. The through-flow measuring cells described therein have an approximately columnar measurement chamber, in which the selected solution medium is preferably fed in from below and pumped through the measurement chamber and then discharged from the measurement chamber at its upper end and fed to a measuring device. An accommodation device for a tablet or granules comprising the active compound, which has, for example, a grid or bowl shape, is usually located in the interior of the measurement chamber. The accommodation device is permanently attached or mounted in the measurement chamber in order to be able to ensure constant geometry and thus comparable measuring conditions even over many measurement series. A measuring cell of this design which is frequently used in practice is described, for example, in U.S. Pat. No. 5,142,920 A.

In order to be able to convert the active compound into tablet form or into granular form, so that measurements with a through-flow measuring cell described above are facilitated, the active compound of interest generally has to be mixed with a suitable assistant which has the physical and in particular mechanical properties necessary for the production of tablets or granules. The active-compound release rate measured in a through-flow cell is accordingly very considerably dependent on the assistant used. It has additionally been found that the active-compound release rate which can be measured in practice is dependent not only on the type or composition of the assistant, but also on other properties, such as, for example, on the pressure used during tablet production or on the ratio of active compound to assistant. In order to be able to compare various measurement results, it is therefore necessary, in spite of the use of extremely uniform through-flow measuring cells, to record and take into account a large number of parameters during the evaluation or comparison of the measurement results for the release rate determined.

In order to be able to measure simply and reliably the internal release rate of an active compound which describes the release of a pure solid substance having ideally negligible porosity and to enable a comparison of the measurement values obtained for the internal release rate, various methods and devices have been developed for the measurement of the internal release rate. In a widely known measurement method, which is likewise monographed in EUROPEAN PHARMACOPOEIA (2.2.29. "intrinsic dissolution"), a pressed disc of an active compound is produced and arranged in a measurement head in such a way that exclusively a circular outer surface of the disc is accessible from the outside. The measurement head is then introduced on a rotatably mounted rod into a storage container containing a solution medium, so that the outside of the disc, which is accessible from the outside, faces downwards in the direction of the base of the storage container. The measurement head rotates during the measurement in order on the one hand to effect uniform mixing of the solution medium and on the other hand to prevent gas bubbles, which could impair the release and dissolution of the active compound and falsify the measurement results, from accumulating at the exposed surface of the pressed disc.

A refinement of this measuring cell is described, for example, in U.S. Pat. No. 6,497,157 B1. In the measuring cell described therein, the pressed disc is arranged in a fixed manner with the exposed surface facing upwards on the base of a container filled with a solvent. A stirrer which mixes the solvent in the storage container during the measurement operation and is intended to prevent local concentration variations or other inhomogeneities is arranged above the pressed disc.

A common feature of the known measuring devices of this type is that, although the internal release rate of a pressed disc comprising an active compound can be measured and an often undesired influence of the binder necessary for tablet production can be prevented, measuring devices of this type usually, however, do not facilitate continuous evaluation, but instead the amount of released active compound dissolved in the solution medium can only be determined after expiry of a pre-defined measurement duration.

Since the monographed measuring devices or those frequently used in practice often have storage containers for the solution medium having a capacity of greater than 200 ml and in some cases up to 4000 ml, the measurements which can be carried out using these measuring devices are material-intensive and expensive. However, the volume of solution medium used in a measurement cannot be specified as small as desired, since in this case the dissolution behaviour of the active compound is already influenced after a short time by the active compound already dissolved owing to the lack of sink conditions.

Besides some of the measuring devices mentioned above, WO2006/108908 A1 describes a further measuring device which is designed as a through-flow measuring cell and can be used for the measurement of the release rate. The solution medium here is transported past the surface of a pressed disc or solidified active compound in the form of a thin film with laminar or turbulent flow. However, the measurement results obtained during a measurement operation cannot readily be compared with the measurement results for the same solid which are determined using other measuring devices, since the external boundary conditions, such as, for example, the flow path of the solution medium in the region around the solidified active compound, differ significantly from those of other measuring devices.

The object of the present invention is accordingly to design a device for carrying out measurements of the internal release rate of an active compound in such a way that precise and comparable measurement results for the determination of the internal release rate can be determined using simple means.

This object is achieved in accordance with the invention in that the device for the accommodation of a solid in a measuring cell mentioned at the outset has an insert which can be introduced into the measuring cell and has a recess for the accommodation of a pressed disc. An insert of this type, which can be introduced in a simple manner into the already known and widely used through-flow measuring cells, enables the use of standardised and monographed through-flow measuring cells for the measurement of the internal release rate of an active compound. The existing measuring cells can be retrofitted in a simple manner and can then also be used for the measurement of the internal release rate. Since through-flow measuring cells of this type are often already available and handling thereof is likewise standardised and known, reliable and reproducible measurement values can be generated using simple means.

The use of a through-flow measuring cell additionally has the major advantage that the solution medium discharged from the measuring cell can be fed continuously to a measuring device and analysed, enabling not only cumulative measurements of the release that has taken place in total after expiry of the measurement duration, but also continuous or differential measurements of the internal release rate.

It is, for example, also possible to change the respective solution medium used at short time intervals, enabling measurement values for various solution media to be obtained in the course of one measurement operation.

The insert can be designed in such a way that the insert can be introduced quickly and reliably into the measuring cell, where it can be arranged or secured in a precisely specified position. Subsequent removal of the insert or the use of changing inserts is thus equally simplified.

It is preferably provided that the recess for the accommodation of the pressed disc is arranged on a side of the insert which faces the inflowing solution medium. Such an arrangement and orientation of the exposed surface of the pressed disc favours a highly uniform interaction of the exposed surface of the pressed disc with the solution medium. In this way, for example, shading effects due to the insert around which the solution medium flows or undesired turbulence, which may form under certain circumstances adjacent to a side of the insert which faces away from the flow, are kept away from the exposed surface of the pressed disc. In the case of the through-flow cells known from practice, in which the solution medium is pumped through the measuring cell from bottom to top, the recess for the accommodation of the pressed disc is advantageously located on the underside of the insert, with the exposed surface of the pressed disc being oriented essentially horizontally.

According to an advantageous embodiment of the inventive idea, it is provided that a wall surface of the insert which surrounds the recess for the accommodation of the pressed disc is tilted in the flow direction, so that the inflowing solution medium is transported laterally away from the pressed disc. The side of the insert which surrounds the pressed disc and faces towards the inflowing solution medium can be designed, for example, as a truncated cone. The inflowing solution medium is transported laterally away from the pressed disc and around the insert by the insert face, which runs obliquely alongside the pressed disc. Owing to the flow conditions forming, the solution medium cannot remain in front of the pressed disc for an extended period. In this way, a fresh solution medium is transported continuously past the pressed disc, meaning that neither locally different concentration ratios nor undesired bubble formation, which could possibly impair the measurement accuracy, are able to form in the region around the pressed disc.

According to an embodiment of the inventive idea, it is provided that the insert has a housing with a hole through it, a sleeve for the accommodation of the pressed disc, which can be accommodated in the hole, and a closure device. The external dimensions of the housing here are advantageously matched to the dimensions of a measurement chamber in the measuring cell. The external diameter of the sleeve is matched to the hole through the housing, meaning that the sleeve can be arranged in the hole with an essentially precise fit. The internal diameter of the sleeve corresponds to the diameter of the pressed disc, which can be arranged and accommodated in the sleeve.

The pressed disc here is advantageously arranged at one end of the sleeve in such a way that the exposed surface of the pressed disc terminates flush with a face of the sleeve and the adjacent wall surfaces of the housing or insert. The closure device tightly seals the sleeve end facing away from the pressed disc, meaning that solution medium cannot enter at the back and come into contact with the pressed disc. The closure device here is advantageously designed in such a way that a plunger-shaped projection of the closure device protrudes into the sleeve and terminates flush with a back surface of the pressed disc.

Various sleeves and closure devices matched in each case to the sleeves, which each have a different internal diameter with a constant external diameter of the sleeves, may be provided. Since the exposed surface of the pressed disc accommodated in the sleeve likewise increases with increasing internal diameter of the sleeve, pressed discs having an exposed surface of different size can be arranged in the same housing and introduced into the measuring cell with the insert. Since the housing can be used for each measurement independently of the size of the pressed disc and only the sleeve arranged in the housing has to be exchanged together with the closure device, precise measurements can be carried out reliably and quickly in this way with exposed pressed-disc surfaces of different size, which measurements can be compared directly with one another owing to the constant housing geometry.

In an advantageous manner, it is provided that the housing and the closure device essentially consist of a plastic material and the sleeve consists of metal. The pressed disc is advantageously produced by compressing the active compound in the sleeve. The pressure forces necessary for this purpose are often so high that the sleeve should advantageously consist of a sufficiently pressure-resistant material, such as, for example, metal, in order to enable, where desired, reliable production of a pressed disc a number of times without the fear of undesired deformation of or even damage to the sleeve.

By contrast, it is advantageous for the housing and the closure device to consist of the lightest possible material, such as, for example, an inert plastic material, and in this way for the total weight of the insert together with the pressed disc accommodated therein to be kept as low as possible. It has been found that, given a suitable shape and choice of material of the individual components of the insert, its total weight can be significantly less than 200 g and weight determinations are possible using commercially available analytical balances, which generally have a highly precise measurement range, but one that is restricted to a maximum weight of 210 g.

In order to be able to carry out visual monitoring and optionally additional optical measurements even while a measurement is being carried out, it is preferably provided that the housing and the closure device are made from a substantially transparent plastic material.

It is preferably provided that the insert has flow channels through which the solution medium can pass through the insert. The flow channels here may be designed on the inside, for example as through-holes, or alternatively formed by cut-outs or grooves at the side. The number, arrangement and respective design of the flow channels can favour a uniform, substantially laminar flow of the solution medium in the environment of the insert and thus in the region of the pressed disc.

The dimensions of the insert here are advantageously matched to the dimensions of the measurement chamber of the measuring cell, meaning that the insert can be arranged quickly and reliably at a constant point within the measurement chamber and is retained in the specified position during the measurement operation, for example by its own weight or by friction.

An illustrative embodiment of the inventive idea which is depicted in the drawing is explained in greater detail below, where:

FIG. 1 shows an exploded view of an insert for a measuring cell,

FIG. 2 shows a likewise exploded sectional view of the insert depicted in FIG. 1, FIG. 3 shows an oblique view of a press device which is suitable for the accommodation of the insert and for the production of a pressed disc, and FIG. 4 shows a diagrammatic representation of a through-flow measuring cell with an insert arranged therein.

An insert 1 depicted in FIGS. 1 and 2 has an essentially hollow-cylindrical housing 2 with a hole 3 arranged in the centre. A sleeve 4 is arranged in the hole 3. Both the hole 3 and the sleeve 4 have at one end an annular recess 5 formed concentrically and projecting to the outside or a projection 6 matched thereto and projecting in an annular manner. In this way, annular stop faces 7, 8 facing one another are formed, by means of which precise relative positioning of the sleeve 4 in the hole 3 can be repeatedly specified and ensured.

The sleeve 4 can be sealed tightly at an end 9 facing away from the flow by means of a screw-shaped closure device 10. The screw-shaped closure device 10 has a region 11 with an external thread 12, which can be engaged with an internal thread 13 matched thereto at the end 9 of the sleeve 4 facing away from the flow, so that the closure device 10 can be screwed into the sleeve 4. The closure device 10 has, in the extension of the region 11 with the external thread 12, a plunger-shaped projection 14, whose external diameter is matched to the internal diameter of the sleeve 4. The closure device 10 can be screwed into the sleeve 4 so far that the plunger-shaped projection 14 substantially fills a cavity 15 in the sleeve 4 and only allows sufficient space at an end 16 of the sleeve 4 facing the flow for the accommodation of a pressed disc, which is not depicted in FIGS. 1 and 2. In the case of a closure device 10 screwed into the sleeve 4, the sleeve 4 and the plunger-shaped projection 14 form a recess 17 for the accommodation of a pressed disc.

Through the use of a press device 18 depicted by way of example in FIG. 3, a pressed disc can be produced in a simple manner directly in the insert 1, which is not depicted in full in FIG. 3. The press device 18 has a flat base plate 19. A lid 21 with a recess 20 which is suitable for the accommodation of the insert 1 can be connected to the base plate 19 by means of screws or other suitable attachment means, so that the insert 1 is arranged between the base plate 19 and the lid 21.

The lid 21 has a hole 22 arranged flush with the sleeve 4 in the insert 1 and matched to the dimensions of the cavity 15 of the sleeve 4. An active compound can be introduced into the cavity 15 of the sleeve 4 through the hole 22 and subsequently compressed by means of a press ram 23, which can be introduced into the cavity 15 of the sleeve 4 through hole 22, to give a pressed disc.

Immediately after the production of the pressed disc, the pressure ram 23 and the lid 21 can be removed and the open end of the sleeve 4 sealed by means of the screw-shaped closure device 10. The plunger-shaped projection 14 of the closure device 10 is introduced here into the cavity 15 of the sleeve 4, and the closure device 10 is screwed together with the sleeve 4, so that the plunger-shaped projection 14 provides a seal for the pressed disc produced beforehand. The insert 1 can subsequently be removed and introduced into a measuring cell with the pressed disc located therein.

FIG. 4 depicts, merely by way of example, a diagrammatic sectional view of the insert 1 described above in a measuring cell 24. The measuring cell 24 is a through-flow measuring cell having an essentially hollow-cylindrical section 25 and a subsequent, conically narrowing filling section 26. A solution medium, not depicted in FIG. 4, can be pumped into a cavity 29 of the measuring cell 24 through an aperture 28, which is usually secured against undesired reflux by means of a ruby glass ball 27. The solution medium pumped into the cavity 29 through the aperture 28 arranged at the bottom is subsequently forced through a number of glass beads 30, so that substantially turbulence-free and essentially laminar flow conditions of the solution medium form in the cavity 29 of the measuring cell 24. The insert 1 is arranged on a region of the hollow-cylindrical section 25 of the measuring cell 24 which faces the aperture 28, with a pressed disc 31 accommodated in the sleeve 4 being arranged at the end 16 of the insert 1 facing the flow in the direction of the glass beads 30. The solution medium is transported past the pressed disc 31 and discharged laterally at wall surfaces 32 of the housing 2 which step back laterally in the manner of a truncated cone and transported past the insert 1 through flow channels 33 and can subsequently be removed and analysed from an upper region 34 of the measuring cell 24.

The invention claimed is:

1. A device for the accommodation of a pressed disc in a measuring cell, in which the release of a solid in the pressed disc can be determined in a solution medium flowing through the measuring cell, comprising:
   an insert that is secured to the interior surface of the measuring cell, the insert comprising
   a housing with a recess for accommodation of the pressed disc, wherein the recess is arranged on a side of the insert which faces an inflowing solution medium,
   wherein the housing forms flow channels between the housing and the inner surface of the measuring cell.

2. The device of claim 1, wherein a wall surface (32) of the insert (1) which surrounds the recess (17) for the accommodation of the pressed disc (31) is tilted in the flow direction, so that the inflowing solution medium is transported laterally away from the pressed disc (31).

3. The device of claim 1, wherein the dimensions of the insert (1) are matched to the dimensions of a measurement chamber (29) of the measuring cell (24).

4. The through-flow measuring cell of claim 1 wherein the pressed disc is arranged at one end of a sleeve in a hole in the housing so that an exposed surface of the pressed disc terminates flush with a face of the sleeve and adjacent wall surfaces of the housing.

5. The device of claim 1, wherein the insert (1) has a housing (2) with a hole (3) through it, a sleeve (4) for the accommodation of the pressed disc (31), which can be accommodated in the hole (3), and a closure device (10).

6. The device of claim 5, wherein the housing (2) and the closure device (10) consist essentially of a plastic material and the sleeve (4) consists of metal.

7. A through-flow measuring cell comprising:
   an insert that is secured to the interior surface of the through-flow measuring cell, the insert comprising
   a housing with a recess for accommodation of a pressed disc, wherein the recess is arranged on a side of the insert which faces an inflowing solution medium,
   wherein the housing forms flow channels between the housing and the inner surface of the measuring cell, and
   wherein the release of a solid can be determined in the solution medium. flowing through the measuring cell.

8. The through-flow measuring cell of claim 7 wherein the pressed disc is arranged at one end of a sleeve in a hole in the housing so that an exposed surface of the pressed disc terminates flush with a face of the sleeve and adjacent wall surfaces of the housing.

9. A through-flow measuring cell having an insert that is secured to the interior surface of the flow cell, the insert further comprising a housing (2) with a hole through it, a sleeve (4) for the accommodation of a pressed disc (31) and which is accommodated in the hole (3), and a closure device (10) couple to the interior of said sleeve, wherein said housing forms flow channels between the housing and the inner surface of the measuring cell.

\* \* \* \* \*

UNITED STATES PATENT AND TRADEMARK OFFICE
CERTIFICATE OF CORRECTION

PATENT NO.       : 8,617,491 B2                                      Page 1 of 1
APPLICATION NO.  : 12/993915
DATED            : December 31, 2013
INVENTOR(S)      : Lange et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 419 days.

Signed and Sealed this
Twenty-second Day of September, 2015

Michelle K. Lee
*Director of the United States Patent and Trademark Office*